United States Patent [19]

Ishida et al.

[11] 4,163,780

[45] Aug. 7, 1979

[54] KS-2-A

[75] Inventors: Nakao Ishida; Fujio Suzuki, both of Sendai; Hiroshi Maeda, Kumamoto; Toshikatsu Fujii, Gotenba; Ituro Mizutani, Numazu, all of Japan

[73] Assignee: Kirin-Seagram Limited, Tokyo, Japan

[21] Appl. No.: 891,767

[22] Filed: Mar. 30, 1978

[30] Foreign Application Priority Data

Mar. 30, 1977 [JP] Japan .................................. 52/35944
Sep. 6, 1977 [JP] Japan ................................ 52/106321

[51] Int. Cl.$^2$ ............................................. A61K 35/00
[52] U.S. Cl. .................................... 424/116; 435/171; 435/811
[58] Field of Search ........................... 424/116; 195/81

*Primary Examiner*—Jerome D. Goldberg
*Attorney, Agent, or Firm*—Browdy and Neimark

[57] ABSTRACT

KS-substance was obtained as raw material from the cultured mycelium of Daedalea dickinsii KSDD 6 (FERM-P No. 3993), Lentinus edodes KSLE 7 (FERM-P No. 3994) or Lentinus edodes KSLE 28 (FERM-P No. 4196), and by refining this substance a novel substance KS-2-A was obtained. This substance KS-2-A and also the KS-substance as the raw material both enhance the host defense function of the living body.

4 Claims, 11 Drawing Figures

This invention relates to a novel substance KS-2-A.

Extensive researches and investigations have been made to inhibit the growth of tumor cells by utilizing some mechanism in a living body which do not have direct cytotoxic effect upon tumor cells but increase host defense function.

The inventors have conducted investigations for obtaining anti-cancer chemotherapeutic agents which are harmless to the normal cell and, as a result, have found a novel substance, namely KS-substance, which is capable of extremely promoting the host defense function and also KS-2-A which is obtained by refining the KS-substance. Further, it has been discovered that KS-2-A has no direct action to tumor cells in vitro, but it has a strong anti-tumor effect in vivo, at least against certain kinds of cancer in the mouse. Furthermore, it has been proved that KS-2-A has prophylactic and chemotherapeutic effects upon many infectious diseases that may be caused by pathogenic micro-organisms and viruses.

KS-2-A can be prepared from cultured mycelim of the micro-organisms.

For example, *Daedalea dickinsii* KSDD 6 (FERM-P No. 3993), *Lentinus edodes* KSLE 7 (FERM-P No. 3994) and *Lentinus edodes* KSLE 28 (FERM-P No. 4196) are used for obtaining KS-2-A. (FERM-P Nos. indicate the microbial strains deposited with Fermentation Research Institute, Agency of Industrial Science and Technology).

As the culture medium, any general medium containing glucose, starch, organic acids etc. as carbon source, polypeptone, yeast extract, urea etc. as nitrogen source, vitamin and inorganic salts may be used. Further, it is effective to add corn steep liquor or distillers solubles. The distillers solubles are obtained as byproduct in the manufacture of grain whisky by sour mash process (Kirk Othmer, "Encyclopedia of Chemical Technology", 2nd Ed. Vol. 1, pages 501 through 531).

The cultured broth is subjected to filtration or centrifugation. The obtained mycelium is subjected to extraction. If desired, finely dividing the obtained mycelium, the extraction is carried out by using hot water or a dilute aqueous salt solution, suitably at 60° to 130° C., preferably 80° to 100° C., containing about 5% of NaCl. The extraction is sufficiently carried out under agitation for about 5 minutes to 3 hours, preferably for 30 to 60 minutes.

The extract is subjected, after separation of solid matter if it is necessary, to a precipitation treatment using an hydrophilic solvent, for instance methanol or ethanol. The resultant precipitate is collected by filtering or centrifugation, followed by lyophilizing to obtain the KS-substance.

This KS-substance is dissolved in water, an equal volume of water-saturated phenol is added to the resultant solution, and the resultant is subjected to violent shaking under cold conditions, thus a water layer is obtained. To this water layer is added water-saturated phenol, and shaking and centrifugal separation are repeated twice. The water layers obtained in this way are combined together, and then ethyl ether is added. The resultant is shaken, and the water layer is collected. Residual ether in the water layer is removed by bubbling with $N_2$ gas.

Four volumes of pure ethanol is added to the resultant water layer. The precipitate thus obtained is dissolved in 0.01 M Tris-HCl buffer (pH 6.95), and the resultant solution is applied to Ecteola cellulose column, which is previously activated and bufferized with the afore-mentioned buffer. The column is eluted with the buffer. Fractions showing the character of KS-2-A are collected, and after dialyzing and lyophilizing, KS-2-A is obtained in the form of white amorphous powder.

Figure 1:
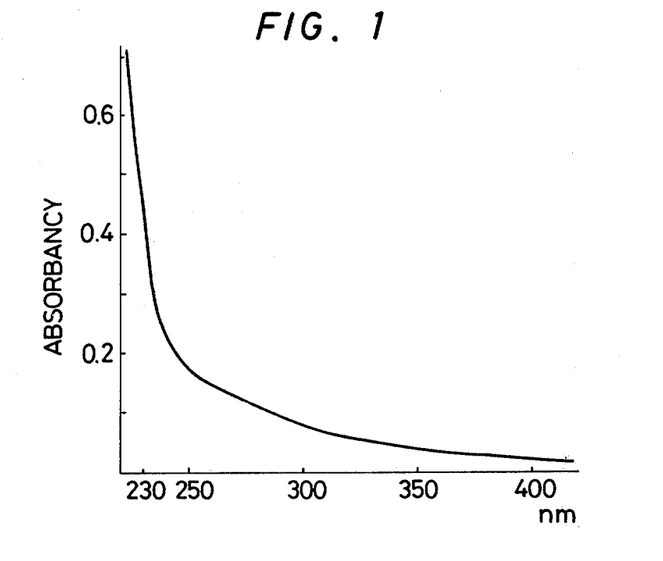
FIG. 1 shows ultraviolet spectrum of KS-2-A.
Figure 2:
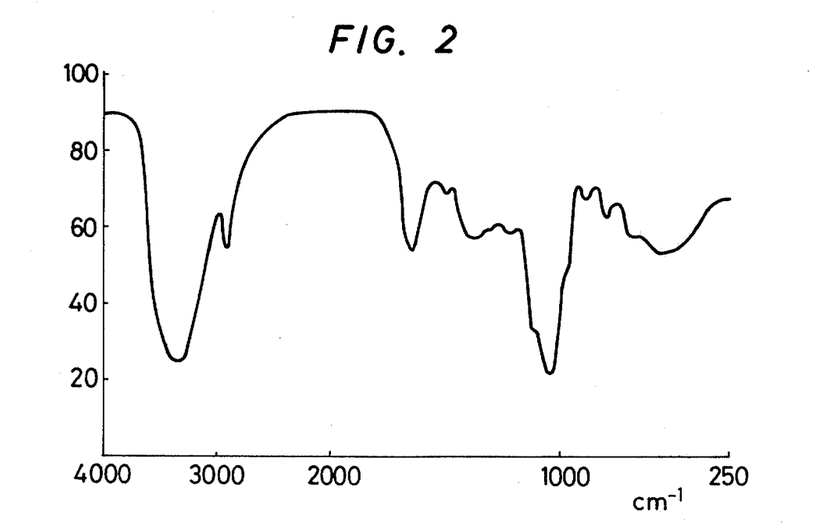
FIG. 2 shows infrared spectrum of KS-2-A.

KS-2-A according to the invention has the following physiochemical properties:

1. Elemental analysis
   C: 39.5%, H: 6.5%, N: 1.1%,
   Ash: trace (0.4%)
2. Molecular weight
   9,000±3,000 (by ultra-filtration)
   7,000 to 9,000 (by equilibrium density gradient centrifugation)
   8,000±3,000 (by fluorescein polarization method)
3. Appearance
   amorphous white powder
4. Decomposition point
   185° C. (based upon measurement of the browning temperature by capillary method using "Silicone Oil WF-30")
5. UV spectrum
   No particular maximal absorption is observed as shown in FIG. 1.
6. IR spectrum
   The spectrum is shown in FIG. 2.
7. The pH of the aqueous solution of this substance is 7.25.
8. Solubility
   Soluble in water, insoluble in ethanol, acetone, n-hexane, n-butanol, phenol and other organic solvents
9. Specific optical rotation $[\alpha]_D^{25} = +67.5 \pm 2.0°$ (in $H_2O$), (C=0.452%)

Figure 3:
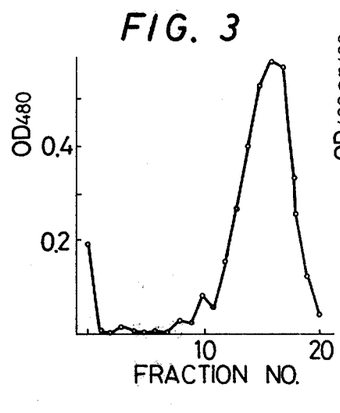
FIG. 3 shows an ultra centrifugation pattern of KS-2-A.

10. Homogeneity
    a. Centrifugation of KS-2-A was made in a linear gradient of 5 to 20% of CsCl in 0.1 M Tris-HCl buffer (pH 7.2) at 38,000 r.p.m., at 4° C. for 15 hours. The result is shown in FIG. 3. As is apparent from the Figure, this substance is homogeneous. The comparative sedimentation experiments with viral nucleic acids showed that this substance does not contain viral particles, RNA or DNA.

b. Electrophoresis was made on cellulose acetate by using 0.1 M acetic acid/pyridine buffer (pH 3.5). Chondroitin sulfate was used as control. After 30 minutes of electrophoresis at 0.6 mA/cm and 160 V, chondroitin sulfate moved to the cathode, giving a mobility of 4 cm per 30 minutes, whereas KS-2-A moved slightly to the anode in 90 minutes (a mobility of 1 cm per 90 minutes), the results being shown in FIG. 4. From the Figure, it is apparent that this substance is electrophoretically homogeneous.

Further, electrophoresis conducted under the same conditions as above except using 1 M pyridine/acetic acid buffer (pH 7.0) proved that this substance is homogeneous.

Figure 5:
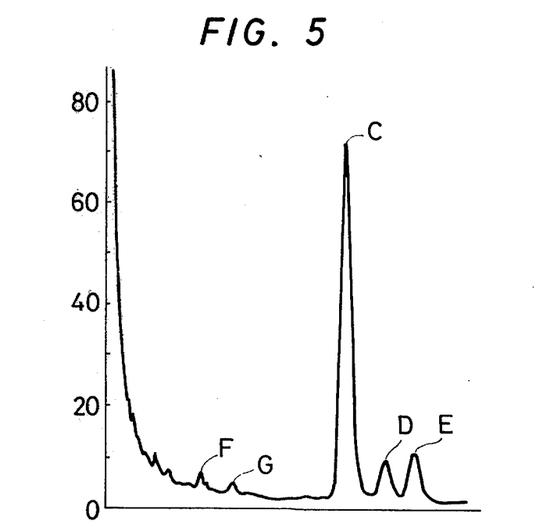
FIG. 5 shows sugar composition analysis (gas chromatography) of KS-2-A (C . . . mannose, D . . . galactose, E . . . glucose, F . . . arabinose, G . . . xylose)

11. Color reaction
Phenol-$H_2SO_4$ reaction: Positive
Anthrone reaction: Positive
Molisch's reaction: Positive
Elson-Morgen reaction: Negative
Carbazole-$H_2SO_4$ reaction: Positive
Reaction with Folin-Ciocarteau reagent: Positive
Biuret reaction: Positive
Reaction with FITC (fluorescein isothiocyanate): Positive
Toluidin blue O staining: Negative
Ninhydrin reaction: Positive
Sugar composition:
KS-2A was subjected to acid hydrolysis, followed by alditolation and then acetylation, and then the sugar composition was determined by gas chromatography. The results are shown in FIG. 5. This substance is mainly composed of mannose and contains small quantities of glucose and galactose and also minute quantities of arabinose and xylose, the proportions of these components by weight being 74:12:12:1:1.

13. Amino acid composition
10 mg of KS-2-A was closed in vacuo together with 3 ml of 6 N HCl added to it, and was subjected to acid hydrolysis at 110° C. for 22 hours. Then HCl was removed by a rotary evaporator, and amino acid analysis was made with the automatic amino acid analyser (HITACHI KLA-3).

The amino acids contained are mainly threonine, serine, glutamic acid, alanine and ammonia, and further slight quantities of aspartic acid, proline, glycine, valine and lysine are contained. Further, sometimes trace amount of methionine, isoleucine, leucine, tyrosine, phenylalanine, histidine, arginine and cystine are recognized.

KS-2-A does not have direct cytotoxic effect on tumor cells. When KS-2-A is given to the living body, it enhances the host defense function of the living body and indirectly restricts the growth of tumor cells, at least with respect to certain tumor cells in mice, thus ultimately eliminating those tumor cells.

In addition, KS-2-A has no bactericidal or virucidal activity. But when KS-2-A is given to the living body it enhances the host defense function of the living body and indirectly inhibits the growth of bacteria or virus in the living body.

Further, KS-2-A can effectively cure man and animals of many infectious diseases, such as influenza, herpes, vaccinia, encephalomyocarditis, infectious hepatitis, rabies, and diseases caused by Pseudomonas, Candida, Listeria, Staphylococcus, Streptococcus, Diplococcus, Neisseria, *Escherichia coli, Mycobacterium tuberculosis,* Spirochaetales and Protozoa. In any event, KS-2-A has both prophylactic and chemotherapeutic effect.

Examples and Experimental Examples of the invention are shown.

EXAMPLE 1

Daedalea dickinsii KSDD 6 (FERM-P No. 3994) was cultured in 10 l of medium containing distillers solubles under aerobic condition of 1.8 vvm at 24° C. for 11 days. The cultured broth was then subjected to centrifugation, whereby 38 g of mycelium was obtained. The mycelium thus obtained was mixed with 10 l of hot 5% NaCl solution, and was boiled for 60 minutes, followed by the separation of supernatant and precipitate. The supernatant thus obtained was mixed with ethyl alcohol so that the final ethyl alcohol concentration was 70%, and allowed to stand overnight in cold dark room. The precipitate was collected and lyophilized to obtain 4 g of KS-substance.

The KS-substance has the following physiochemical properties.

Figure 6:
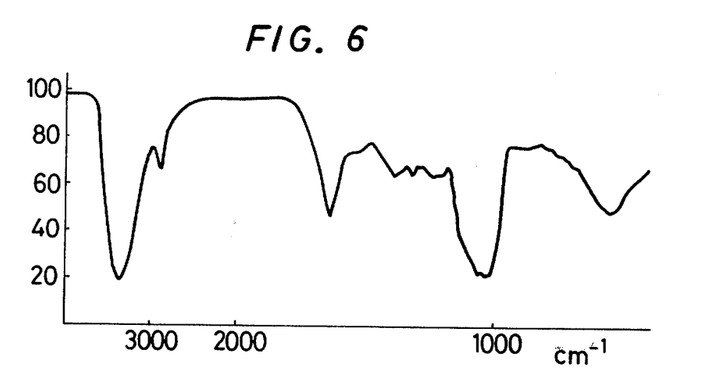
FIG. 6 shows infrared spectrum of KS-substance.
Figure 7:
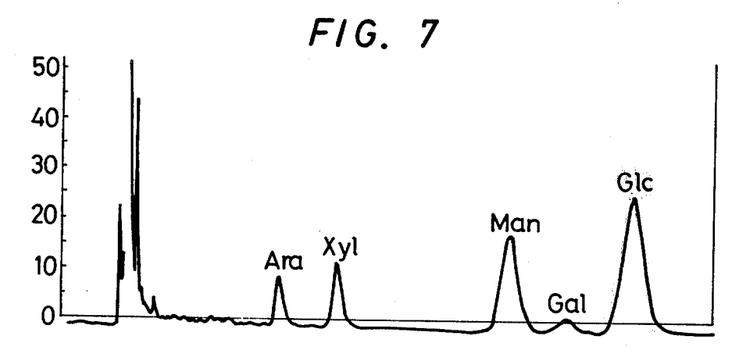
FIG. 7 shows sugar composition analysis (gas chromatography) of KS-substance.
Figure 8:
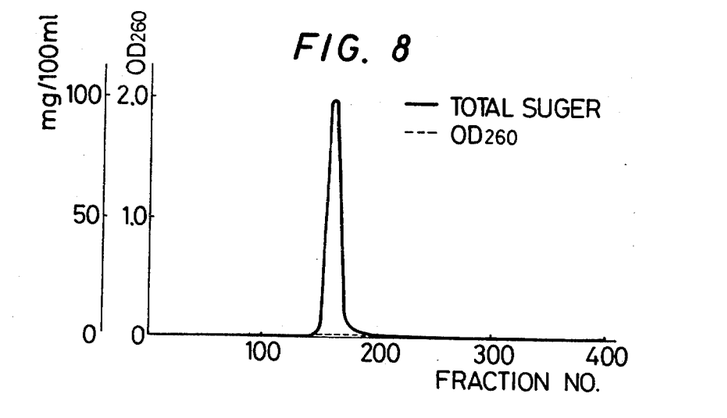
FIG. 8 shows elution pattern of Ecteola cellulose column in Example 3.

1. Elemental analysis (by C.H.N. meter): C: 18.6±2.3%, H: 2.8±0.4%, N: 1.3±0.2%, Ash: 10.5±1.3%.
2. Molecular weight (determined by Biogel P-series column and Amicon ultra-filtration): About 70,000
3. Decomposition point: 300°0 C. or above
4. IR spectrum: As shown in FIG. 6
5. Solubility: Soluble in water, insoluble in ethanol, n-butanol, acetone and hexane
6. Color reaction (with 1% aqueous solution of KS-substance):
Anthron reaction: Positive
Morgan-Elson reaction: Negative
Carbazole-$H_2SO_4$ reaction: Positive
7. The pH of the aqueous solution of KS-substance is 6 to 7.
8. Appearance: Amorphous white powder
9. Amino acid composition (in g per 100 g):
Arginine: 0.4±0.05, Lysine: 0.5±0.06,
Histidine: 0.4±0.05, Phenylalanine: 0.2±0.03,
Tyrosine: 0.2±0.03, Leucine: 0.3±0.04,
Isoleucine: 0.3±0.04, Methionine: 0.1±0.01,
Valine: 0.4±0.05, Alanine: 0.6±0.08,
Glycine: 0.8±0.1, Proline: 0.6±0.08,
Glutamic acid: 1.2±0.2, Serine: 1±0.1,
Threonine: 0.8±0.1, Aspartic acid: 1±0.1,
Tryptophane: 0.06±0.01, Cystine: 0.3±0.04
10. Sugar composition (determined by gas chromatography):
Glucose: 57±6%, Galactose: 5±0.5%,
Mannose: 26±3%, Xylose: 8±0.8%,
Arabinose: 5±0.3%

EXAMPLE 2

The KS-substance obtained in Example 1 was dissolved in water, and an equal volume of water-saturated phenol was added to the solution. The mixture was shaken under cold conditions and then subjected to centrifugation to obtain a water layer. To this water layer was added water-saturated phenol, and shaking and centrifugal separation were repeated twice. The water layers obtained in this way were combined together, and then ethyl ether was added. The resultant was shaken, and the water layer was collected. The residual ether in the water was removed by bubbling with $N_2$ gas. Four volumes of pure ethanol was added to the water layer obtained. The mixture was allowed to stand overnight in a cold dark room. The precipitate thus obtained was dissolved in 0.01 M Tris-HCl buffer (pH 6.95), and the resultant solution was applied to Ecteola cellulose column, which had been previously activated and bufferized with the afore-mentioned buffer. The column was then eluted with the same buffer. Fractions showing the character of KS-2-A were collected, and after dialyzing and lyophilizing to obtain 0.7 g of KS-2-A.

EXAMPLE 3

Lentinus edodes KSLE 28 (FERM-P No. 4196) was cultured by shaking in a medium containing distillers solubles at 24° C. for 14 days, and the resultant culture broth was inoculated into 10 l of the medium obtained by diluting distillers solubles to a specific gravity of 1.012 to 1.020 and cultured at 24° C. under aerobic condition (1.8 vvm) for 11 days. The resultant broth was then subjected to centrifugation, whereby 38 g of mycelium was obtained.

The mycelium thus obtained was mixed with 10 l of hot 5% NaCl solution, and was boiled for 60 minutes, followed by the separation of supernatant and precipitate. The supernatant thus obtained was mixed with ethyl alcohol so that the final ethyl alcohol concentration was 70% and allowed to stand overnight in cold dank room. Thus the precipitate of KS-substance was obtained.

The KS-substance obtained above was dissolved in water, and an equal volume of water-saturated phenol was added to the solution. The resultant was shaken under cold conditions and then subjected to centrifugation to obtain a water layer. To this water layer was added water-saturated phenol, and shaking and centrifugal separation were repeated twice. The water layers obtained in this way were combined together, and then ethyl ether was added. The resultant was shaken, and the water layer was collected. Residual ether in the water layer was removed by bubbling with $N_2$ gas.

Four volumes of pure ethanol was added to the resultant water layer. The resultant was allowed to stand overnight in a cold dark room.

The precipitate thus obtained was dissolved in 0.01 M Tris-HCl buffer (pH 6.95), and the resultant solution was applied to Ecteola cellulose column, which had been previously activated and bufferized with the afore-mentioned buffer. The column was eluted with the buffer. Fractions showing the character of KS-2-A were collected, dialyzed and lyophilized. Thus 0.7 g of KS-2-A was obtained.

Experimental Example 1

Ascites tumor cells of sarcoma 180 were taken out by an injector and diluted ten-fold with saline. The suspension thus prepared was intramuscularly injected into left thigh of 40 DDI mice (♂ ♀) by 0.1 ml ($10^7$ cells per 0.1 ml) for each mouse. After 24 hours, KS-2-A obtained in Example 3 was dissolved in saline and orally administered 12 times at an interval of 24 hours to four groups of mice, each group consisting of eight mice, as much as 100 mg/Kg, 10 mg/Kg, 1 mg/Kg and 0.1 mg/Kg at a time for each mouse in the respective groups. The control group mice were orally administered with saline alone in the same schedule and in the same manner. Seven weeks after the first KS-2-A administration, the individual mice were killed, and the weight of removed tumor parts was measured.

The results are shown in the Table below.

Table

| Dose (mg/kg) | Tumor weight (g) | Average of tumor weight (g) | Mortality (%) | Index* |
|---|---|---|---|---|
| 100 | 1.0, 0.3, 0.2, 0.15 trace in 4 other mice | 0.21 | 50 | 0.09 |
| 10 | 0.05, 0.4, trace in 6 other mice | 0.05 | 25 | 0.02 |
| 1 | trace in all 8 mice | 0 | 0 | 0 |
| 0.1 | 3.4, 2.6, 4.8, 6.8 trace in 4 other mice | 2.20 | 50 | 1.01 |
| Control (saline) | 1.8, 3.0, 0.7, 3.4 1.8, 2.3, 2.0, 2.5 | 2.17 | 100 | 1.00 |

Figure 9:
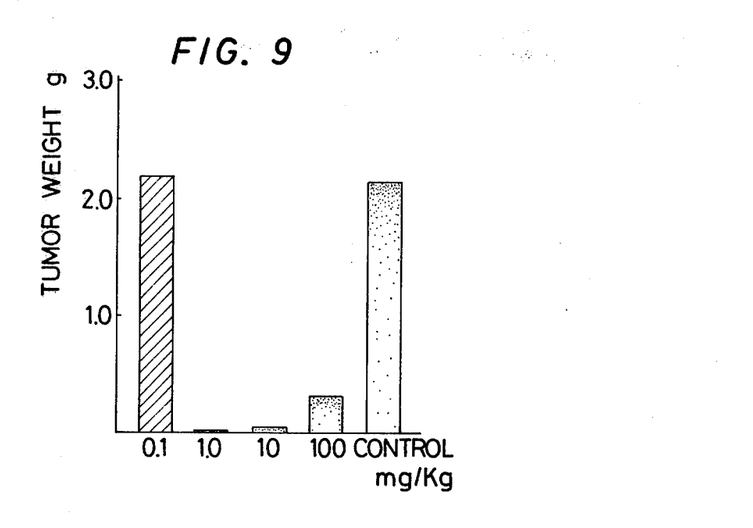
FIG. 9 is a graph showing the relation between the dose of KS-2-A and the tumor weight.

*Index = Average of tumor weight of treated group/Average of tumor weight of control group The above results are shown in FIG. 9.

Similar results as above were obtained with KS-substance.

Experimental Example 2

24 hours after 200 mg/Kg of KS-2-A was intraperitoneally or orally administered once to mice, $10^3$ Ehrlich ascites tumor cells were intraperitoneally inoculated into each mouse. The number of their survival days was observed.

DDI mice (♂, ♀) with body weight of 20 g and about 6-week-old were used in this experiment.

The results are shown in the Table below.

Table

| Route of administration | Number of mice | Survival days | Average of survival days | Survival/treated (%) |
|---|---|---|---|---|
| Intraperitoneal | 10 | 23, 27, 28, 29, 29, 30, >100, >100, >100, >100 | >56.6 | 4/10 (40) |
| per OS | 10 | 26, 26, 27, 27, 28, 30, 30, >100, >100, >100 | >49.4 | 3/10 (30) |
| Control (saline) | 10 | 22, 23, 24, 25, 25, 25, 25, 26, 26, 26 | 24.7 | 0/10 (0) |

Similar results as above were obtained with KS-substance.

Experimental Example 3

Ehrlich ascites tumor cells taken out from mouse were washed several times with serum-free RPMI-1640 medium for 5 minutes at 1,800 r.p.m., and cell concentration was adjusted to $1 \times 10^4$ cells/ml by using the same medium.

Meanwhile, KS-2-A was dissolved in the same medium to prepare solutions of 10 mg/ml, 2 mg/ml and 400 mcg/ml. 1 ml of each KS-2-A solution thus prepared was added to 1 ml of the afore-mentioned Erlich cell suspension, and cultivated in $CO_2$ incubator for 2 hours at 37° C. During the cultivation, the test tube was shaken several times.

Thereafter, each culture was centrifuged at 1,800 r.p.m. for 5 minutes, followed by washing with the RPMI-1640 medium. Cell pellets obtained in this way were suspended in 2 ml of the medium. 0.2 ml of each suspension thus obtained was intraperitoneally administered into 5 DDI 6-week-old mice in each group.

The number of survival days was observed. The results are shown in the Table below.

It is shown that the survival days in the individual groups are practically the same as in the control group, indicating that KS-2-A has no direct cytotoxic activity with respect to the cancer cell.

Table

| Treatments | Number of mice | Survival days | Average of survival days | Survival/treated |
|---|---|---|---|---|
| KS-2-A 10 mg/ml | 5 | 24, 24, 25, 26, 30 | 25.8 | 0/5 |
| KS-2-A 2 mg/ml | 5 | 26, 26, 27, 28, 31 | 27.6 | 0/5 |
| KS-2-A 400 mcg/ml | 5 | 25, 25, 25, 30, 30 | 27.0 | 0/5 |
| RPMI-1640 (Control) | 5 | 24, 25, 26, 28, 32 | 27.0 | 0/5 |

Experimental Example 4

DDI mice (with body weight of 20 g and 6-week-old) was intraperitoneally administered with 200 mg/Kg of KS-2-A, and 24 hours afterwards peritoneal exudate cells were washed out with serum-free RPMI-1640 medium. The washed exudate cells were cultured in a $CO_2$ incubator for 2 hours. Thereafter, non-adherent cells were discarded, and the adherent cells were washed two or three times with RPMI-1640 medium warmed at 37° C. The cells persistently adhered to the petri dish were collected by using trypsin and EDTA, and the macrophage derived from KS-2-A-treated mouse was obtained.

Meanwhile, Ehrlich ascites tumor was intraperitoneally inoculated into other DDI 6-week-old mice by $10^3$ cells per mouse. To these mice the afore-mentioned macrophage was intraperitoneally inoculated 24 hours before the tumor inoculation, thereafter, at intervals of 3 days, 10 times in total, at a rate of $5 \times 10^5$ to $1 \times 10^6$ cells per inoculation. The number of survival days of these mice was observed.

The results are shown in the Table below.

Table

| Treatment of tumor-bearing mice | Number of mice | Survival days | Average of survival days | Survival (%) |
|---|---|---|---|---|
| KS-2-A-treated mouse macrophage | 10 | 26, 40, 43, 45, 46, >100, >100, >100, >100, >100 | >70.0 | 5/10 (50) |
| Non-treated mouse macrophage | 10 | 24, 26, 27, 28, 29, 30, 31, 32, 34, 35 | 29.6 | 0/10 (0) |
| RPMI-1640 medium alone | 10 | 26, 26, 27, 28, 28, 28, 29, 29, 30, 31 | 28.2 | 0/10 (0) |

Experimental Example 5

Transformed established cell line of FM-3A prepared at $1 \times 10^5$ cells/ml with Eagle's MEM medium supplemented with 10% FCS (fetal calf serum) was charged in three different culture bottles (a), (b) and (c).

Bottle (a) was cultured without any addition of macrophage.

Bottle (b) was cultured in the presence of $1 \times 10^6$ cells/ml of the non-activated macrophage obtained in Experimental Example 4.

Bottle (c) was cultured in the presence of $1 \times 10^6$ cells/ml of the macrophage derived from KS-2-A-treated mouse obtained in Experimental Example 4.

The cultivation was made at 37° C., under 5% $CO_2$ condition for 72 hours. After 24, 48 and 72 hours, the numbers of FM-3A cells were counted by haemocytometer.

Figure 10:
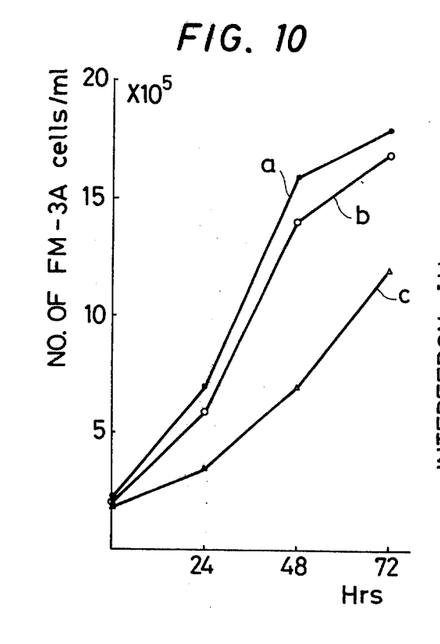
FIG. 10 shows the growth of FM-3A in Experimental Example 5 (a . . . control, b . . . cultured with non-activated macrophage, c . . . cultured with activated macrophage)

The results are shown in FIG. 10, and it will be seen that the macrophage activated by KS-2-A has the effect of inhibiting the growth of cancer cells.

Experimental Example 6

40 DDI mice with average body weight of 22 g were intraperitoneally administered with 200 mg/Kg of KS-2-A (group I).

Other 40 DDI mice were orally administered with 500 mg/Kg of KS-2-A (group II)

After 4, 8, 12, 16, 20, 24, 28 and 32 hours, 5 mice were picked up from each group and sacrificed to extract blood. The blood thus obtained was centrifuged at 3,000 r.p.m. for 10 minutes to obtain serum.

Figure 11:
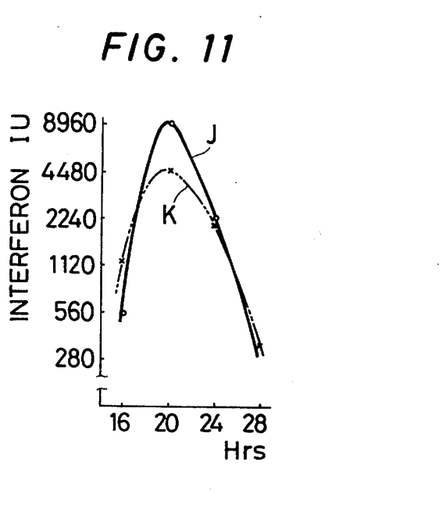
FIG. 11 shows the relation between the time after administration of KS-2-A and the quantity of circulating interferon induced (J . . . intraperitoneal administration of 200 mg/kg, K . . . oral administration of 500 mg/kg).

Titer of interferon was measured in the thymidinekinase less strain of mouse L-1D cell and vesicular stomatitis virus (VSV). Interferon titer was obtained by definite protection of viral cytopathic effect (CPE) caused by the diluted blood serum. Indicated titer of interferon was calibrated by referring to International unit of interferon provided by the National Institute of Health (NIH) in U.S.A. The results are shown in FIG. 11. It will be seen that the circulating interferon is induced about 20 hours after the administration of KS-2-A.

Experimental Example 7

Four groups of DDI mice (with average body weight of 20 g and about 6-weeks-old) were intraperitoneally administered with 200, 100, 50 and 25 mg/Kg of KS-2-A. Each group was composed of 5 mice. 24 hours after the administration, blood was extracted from each group of mouse for determining the titer of circulating interferon. The results are shown in the Table below.

Table

| Intraperitoneal dose of KS-2-A | Interferon titer/ml |
|---|---|
| 200 | 800 |
| 100 | 800 |
| 50 | 800 |
| 25 | 800 |

These interferon samples showed general properties of interferon such as trypsin sensitivity, host species specificity etc.

Experimental Example 8

Listeria monocytogenesis isolated from patient with Listerial infection was suspended in distilled water by $10^8$ viruses/ml and injected for infection into mice in tail vein thereof by 0.1 ml/mouse. 24 hours before the injection of Listeria, 0.5 ml of KS-2-A solution was intraperitoneally administered. Dose level of KS-2-A was 5 to 425 mg/Kg for individual mice in various groups. Control mice were intraperitoneally administered with 0.5 ml saline. Number of mice survived for 20 days after the infection was observed, and survival percentage was calibrated.

The results are shown in the Table below.

| Intraperitoneal dose of KS-2-A (mg/Kg) | Number of mice | Number of survivals after 20 days | Survival percentage (%) |
| --- | --- | --- | --- |
| 425 | 7 | 7 | 100 |
| 141 | 7 | 7 | 100 |
| 47 | 8 | 8 | 100 |
| 16 | 8 | 7 | 87.5 |
| 5 | 8 | 8 | 100 |
| 0 (Control) | 19 | 5 | 26.3 |

Experimental Example 9

The same treatment as in the Experimental Example 8 was made except for that 5 to 425 mg/Kg of KS-2-A was orally administered. Number of mice survived for 20 days after the infection was observed, and survival percentage was calibrated.

The results are shown in the Table below.

Table

| Oral dose of KS-2-A (mg/Kg) | Number of mice | Number of survivals after 20 days | Survival percentage (%) |
| --- | --- | --- | --- |
| 425 | 7 | 7 | 100 |
| 141 | 8 | 7 | 87.5 |
| 47 | 8 | 7 | 87.5 |
| 16 | 8 | 8 | 100 |
| 5 | 8 | 7 | 87.5 |
| 0 (Control) | 19 | 5 | 26.3 |

Experimental Example 10

*Pseudomonas aeruginosa* isolated from the urine of leukemia patient was cultured at 37° C. for 24 hours, and then it was suspended in distilled water by $10^8$ viruses/ml and injected for infection into 26 DDI mice (female, with body weight of 20 g and 6-week-old) in tail vein thereof by 0.1 ml/mouse.

24 hours before the injection, 150 mg/Kg of KS-2-A was intraperitoneally administered in 0.5 ml aqueous solution for the treated group, while 0.5 mg of saline was intraperitoneally administered for control group. Number of mice survived for 20 days after the infection was observed, and survival percentage was determined. The results are shown in the Table below.

Table

| Dose of KS-2-A (mg/Kg) | Number of mice | Survived days | Average of survival days | Number of survivals after 20 days | Survival percentage (%) |
| --- | --- | --- | --- | --- | --- |
| 150 | 14 | 2, 2, 3, 3, >14, >14, >14, >14, >14, >14, >14, >14, >14 >14 | >10.7 | 10 | 71 |
| 0 (control) | 12 | 1, 1, 1, 1, 2, 2, 3, 3, 3, 3, 4, 4 | 2.3 | 0 | 0 |

Experimental Example 11

Direct anti-bacterial activities of KS-2-A were examined by pulp disc diffusion method using various bacteria and 1,000 mcg/ml of KS-2-A aqueous solution. As shown in the Table below, KS-2-A did not show direct anti-bacterial activity.

Table

| Microbe tested | MIC (minimum inhibitory concentration) |
| --- | --- |
| Pseudomonas aeruginosa | >1,000 mcg/ml |
| Klebsiella pneumoniae | >1,000 mcg/ml |
| Listeria monocytogenes | >1,000 mcg/ml |
| Escherichia coli | >1,000 mcg/ml |
| Staphylococcus aureus209-P | >1,000 mcg/ml |
| Candida albicans | Candida 1,000 mcg/ml |
| Candida tropicalis | >1,000 mcg/ml |
| Candida pseudotropicalis | >1,000 mcg/ml |
| Candida utilis | >1,000 mcg/ml |
| Saccharomyces cerevisiaeBr-60 | >1,000 mcg/ml |
| Hansenula anomala | >1,000 mcg/ml |
| Proteus OX-19 | >1,000 mcg/ml |
| Bacillus subtilis | >1,000 mcg/ml |
| Shigella sonnei | >1,000 mcg/ml |
| Sarcina lutea | >1,000 mcg/ml |

Experiment Example 12

DDI mice with body weights ranging from 14 to 16 g infected intranadelly with influenza virus were intravenouslly or orally administered with 200 mg/Kg of KS-2-A. For control, 50 mg/Kg of virazole or 0.5 ml of saline was intraperitoneally administered. Survival days and survival percentage of mice were determined. Both KS-2-A and virazole were administered as respective solutions in saline a total of 15 times, namely one hour before the virus infection, at the time thereof, 1, 3 and 6 hours after the infection and thereafter twice a day for 4 days. As influenza virus, mouse-adapted strain of influenza $A_2$-Kumamoto/$Y_5(H_2N_2)$ virus was challenged at 10 $LD_{50}$ dose. The results are summarized in the Table below.

Table

| Drug | Route of administration | Number of mice | Average of survival days | Survival percentage (%) |
| --- | --- | --- | --- | --- |
| KS-2-A, 200 mg/Kg | Intraperitoneal | 25 | >20 | 52 |
| KS-2-A, 200 mg/Kg | Oral | 25 | >19 | 32 |
| Virazole, 50 mg/kg | Intraperitoneal | 20 | >16.9 | 30 |
| Control | Intraperitoneal | 50 | 9.2 | 0 |

Experimental Example 13

Toxicity of KS-2-A was examined. The results are as shown in the Table below.

Table

| Test animal | Intraperitoneal administration | Oral administration | Intravenous administration |
|---|---|---|---|
| Mouse $LD_{50}$(mg/Kg) | 2,083 | >12,500 | 875 |
| Rat $LD_{50}$(mg/Kg) | — | >2,000 | — |
| Guinea peg $LD_{50}$(mg/Kg) | >600 | >2,000 | — |

Figure 4:
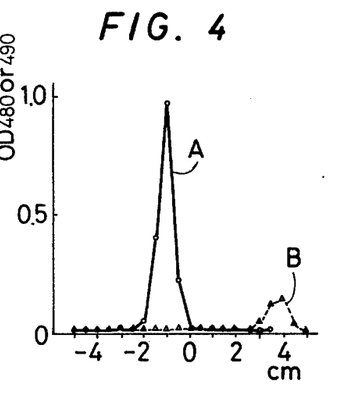
FIG. 4 shows an electrophoretic pattern of KS-2-A (A . . . KS-2-A, B . . . chondroitin sulfate as a control)

What is claimed is:

1. KS-2-A having the following physicochemical properties:
    (1) Elemental analysis
        C: 39.5%, H: 6.5%, N: 1.1%,
        Ash: trace (0.4%);
    (2) Molecular weight
        9,000±3,000 (by ultra-filtration),
        7,000 to 9,000 (by equilibrium density gradient centrifugation),
        8,000±3,000 (by fluorescein polarization method);
    (3) Appearance
        amorphous white powder;
    (4) Decomposition point
        185° C. (based upon measurement of the browning temperature by capillary method using "Silicone Oil WF-30");
    (5) UV spectrum
        No particular maximal absorption is observed as shown in FIG. 1;
    (6) IR spectrum
        The spectrum is shown in FIG. 2;
    (7) The pH of the aqueous solution of this substance is 7.25;
    (8) Solubility
        Soluble in water, insoluble in ethanol, acetone, n-hexane, n-butanol, phenol and other organic solvents;
    (9) Specific optical rotation
        $[\alpha]_D^{25} = +67.5° \pm 2.0°$ (in $H_2O$), (C=0.452%);
    (10) Homogeneity
        a. The result of centrifugation in a linear gradient of 5 to 20% of CsCl in 0.1 M Tris-CHl buffer (pH 7.2) at 38,000 r.p.m., at 4° C. for 15 hours is shown in FIG. 3, the substance being homogeneous as is apparent from the Figure; comparative sedimentation experiments with viral nucleic acids show that the substance does not contain viral particles, RNA or DNA;
        b. The substance is electrophoretically homogeneous as is shown in FIG. 4 which shows the results of electrophoresis on cellulose acetate using 0.1 M acetic acid/pyridine buffer (pH 3.5), chondroitin sulfate being used as control; after 30 minutes of electrophoresis at 0.6 mA/cm and 160 V, chondroitin sulfate moves to the cathode, giving a mobility of 4 cm per 30 minutes, whereas KS-2-A moves slightly to the anode in 90 minutes (a mobility of 1 cm per 90 minutes); the substance is also shown to be homogeneous by electrophoresis conducted under the same conditions as above except using 1 M pyridine/acetic acid buffer (pH 7.0);
    (11) Color reaction
        Phenol-$H_2SO_4$ reaction: Positive
        Anthrone reaction: Positive
        Molisch's reaction: Positive
        Elson-Morgen reaction: Negative
        Carbazole-$H_2SO_4$ reaction: Positive
        Reaction with Folin-Ciocarteu reagent: Positive
        Biuret reaction: Positive
        Reaction with FITC (fluorescein isothiocyanate): Positive
        Toluidin blue O staining: Negative
        Ninhydrin reaction: Positive;
    (12) Sugar composition
        FIG. 5 shows the results of subjecting the substance to acid hydrolysis, followed by alditolation and then acetylation, and then determining the sugar composition by gas chromatography; the substance is mainly composed of mannose and contains small quantities of glucose and galactose and also minute quantities of arabinose and xylose, the proportions of these components by weight being 74:12:12:1:1; and
    (13) Amino acid composition
        Amino acid analysis, made in an automatic amino acid analyzer after closing 10 mg of the substance in vacuo together with 3 ml of 6 N HCl, subjecting it to acid hydrolysis at 110° C. for 22 hours and then removing by a rotary evaporator shows that the amino acids contained are mainly threonine, serine, glutamic acid, alanine and ammonia, and further slight quantities of aspartic acid, proline, glycine, valine and lysine are contained; further, sometimes trace amounts of methionine, isoleucine leucine, tyrosine, phenylalanine, histidine, arginine and cystine are recognized.

2. A chemotherapeutic agent comprising an interferon titer increasing effective amount of KS-2-A in accordance with claim 1 as active component and a pharmaceutically acceptable carrier.

3. A method for manufacturing KS-2-A in accordance with claim 1 comprising culturing a strain selected from a group consisting of Daedalea dickinsii KSDD 6 (FERM-P No. 3993), Lentinus edodes KSLE 7 (FERM-P No. 3994) and Lentinus edodes KSLE 28 (FERM-P No. 4196) in a medium consisting essentially of distillers solubles under aerobic conditions until a substantial amount of KS-2-A is accumulated in the culture broth.

4. A method for increasing the interferon titer of a patient comprising administering to said patient an interferon titer increasing effective amount of KS-2-A as defined in claim 1.

* * * * *